(12) United States Patent
DePetrillo

(10) Patent No.: US 6,342,400 B1
(45) Date of Patent: Jan. 29, 2002

(54) DYE PENETRANT TEST FOR SEMICONDUCTOR PACKAGE ASSEMBLY SOLDER JOINTS

(75) Inventor: Kevin M. DePetrillo, San Jose, CA (US)

(73) Assignee: Advanced Micro Devices, Inc., Sunnyvale, CA (US)

(*) Notice: Subject to any disclaimer, the term of this patent is extended or adjusted under 35 U.S.C. 154(b) by 0 days.

(21) Appl. No.: 09/543,348

(22) Filed: Apr. 5, 2000

(51) Int. Cl.$^7$ .................. G01R 31/26; H01L 21/66; H01L 21/44

(52) U.S. Cl. .............. 438/15; 438/14; 438/16; 438/108; 228/105

(58) Field of Search ................. 438/14, 15, 16, 438/108; 228/103, 105; 224/537, 758

(56) References Cited

U.S. PATENT DOCUMENTS

| 4,230,754 A | * | 10/1980 | Maher et al. | .............. 428/76 |
| 5,651,493 A | * | 7/1997 | Bielick et al. | ............ 228/105 |
| 6,117,352 A | * | 9/2000 | Weaver et al. | ............ 216/105 |
| 6,117,695 A | * | 9/2000 | Murphy et al. | .............. 438/15 |

OTHER PUBLICATIONS

Levis et al., Assembly and Solder Joint Reliability of Plastic Ball Grid Array with Lead–Free Versus Lead–Tin Interconnect, 2000 Electronic Components and Technology Conference, pp 1198–1204.*

* cited by examiner

Primary Examiner—Richard Elms
Assistant Examiner—Adam Pyonin
(74) Attorney, Agent, or Firm—McDermott, Will & Emery

(57) ABSTRACT

A method is provided for inspecting solder-bumped joints of a semiconductor package assembly comprising a packaged semiconductor device and a substrate, such as a circuit board. Embodiments include immersing the package assembly in a dye solution, such as red tracer dye, then placing the immersed package assembly under a vacuum such that, when cracks exist between the solder bumps and substrate bonding pads, or between the solder bumps and the semiconductor device bonding pads, the dye solution flows into the cracks. The package assembly is removed from the vacuum and the dye solution, dried, and the semiconductor device and the substrate manually separated. Thereafter, the substrate bonding pads and the semiconductor device bonding pads are inspected, as with an optical microscope, for residual dye, indicating cracked solder joints. Thus, cracked solder joints, and the full extent of the cracks, are clearly indicated by the presence of dye on the bonding pads after the inventive procedure is performed.

9 Claims, 3 Drawing Sheets

DYE PENETRANT TEST FOR SEMICONDUCTOR PACKAGE ASSEMBLY SOLDER JOINTS

FIELD OF THE INVENTION

The present invention relates to a method for testing the integrity of soldered joints in semiconductor package assemblies. The present invention has particular applicability in testing the joint adhesion of fine-pitched ball grid array (FBGA) packages to a substrate.

BACKGROUND ART

In conventional electronic circuit board assembly techniques known as "solder bumping", the circuit board, such as a laminated printed circuit board (PCB), is provided with an array of bonding pads, such as fine-pitched round metal bonding pads, and a packaged semiconductor device, such as an integrated circuit in a molded plastic package known as a fine-pitched ball grid array (FBGA), is provided with a corresponding array of comparably sized and shaped bonding pads. A solder preform called a "solder ball" is placed between each of the bonding pads of the circuit board and a corresponding bonding pad of the semiconductor device, and then the assembly is heated, as in an oven, to melt (or "reflow") the solder balls, each of which adhere to its respective pair of bonding pads to establish electrical contact between the circuit board and the semiconductor device, and to hold the semiconductor device in place on the circuit board.

Due to the limitations of the solder bumping process, one or more of the solder balls occasionally do not wet properly to their bonding pads during reflow, resulting in cracks in the joint between those solder bumps and the improperly-wetted bonding pads. Cracks also occur during stress testing (i.e., heat cycling) of the assembled circuit board. Cracks are disadvantageous to the extent they result in partial or completely open circuits, and consequent failure of the assembled board. Therefore, the quality of the solder bumping process is typically monitored to detect cracks. Conventional inspection techniques involve cross-sectioning an assembled circuit board. However, this method has drawbacks, in that it is time-consuming and does not test all bonds to determine solder bump bond strength. Furthermore, other conventional inspection techniques involving acoustic microscopy and x-rays cannot detect cracks.

There exists a need for an accurate, low-cost methodology for inspection of all the solder joints of solder-bumped circuit board assemblies.

SUMMARY OF THE INVENTION

An advantage of the present invention is an accurate and reliable method of inspecting all the solder joints of a semiconductor package assembly.

Additional advantages and other features of the present invention will be set forth in part in the description which follows and in part will become apparent to those having ordinary skill in the art upon examination of the following or may be learned from the practice of the invention. The advantages of the invention may be realized and obtained as particularly pointed out in the appended claims.

According to the present invention, the foregoing and other advantages are achieved in part by a method of inspecting solder joints of a semiconductor package assembly, the package assembly comprising a substrate with bonding pads, a semiconductor device with bonding pads, and solder bumps attached between each substrate bonding pad and a corresponding bonding pad of the semiconductor device, the method comprising immersing the package assembly in a solution comprising dye; placing the immersed package assembly under a vacuum such that, when cracks exist between the solder bumps and substrate bonding pads, or between the solder bumps and the semiconductor device bonding pads, the dye solution flows into the cracks; removing the package assembly from the vacuum and the dye solution; drying the package assembly; separating the semiconductor device and the substrate to expose a plurality of the substrate bonding pads or the semiconductor device bonding pads; and inspecting the exposed bonding pads for the dye, thereby locating the cracks.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Conventional methodologies for inspecting solder joints of a semiconductor package assembly are time-consuming, and do not provide accurate and reliable data on all of the joints. The present invention addresses and solves these problems stemming from conventional inspection procedures.

According to the methodology of the present invention, solder-bumped joints of a semiconductor package assembly comprising a packaged semiconductor device and a substrate, such as a circuit board, are inspected by immersing the package assembly in a dye solution, such as red tracer dye, then placing the immersed package assembly under a vacuum such that, when cracks exist between the solder bumps and substrate bonding pads, or between the solder bumps and the semiconductor device bonding pads, the dye solution flows into the cracks. The package assembly is removed from the vacuum and the dye solution, and then dried. The semiconductor device and the substrate are thereafter manually separated. The substrate bonding pads and the semiconductor device bonding pads are inspected, as with an optical microscope, for residual dye, indicating cracked solder joints. Thus, the present methodology clearly points out any cracked solder joints, and the full extent of the cracks, by the presence of dye on the bonding pads after the inventive procedure is performed.

Figure 1:
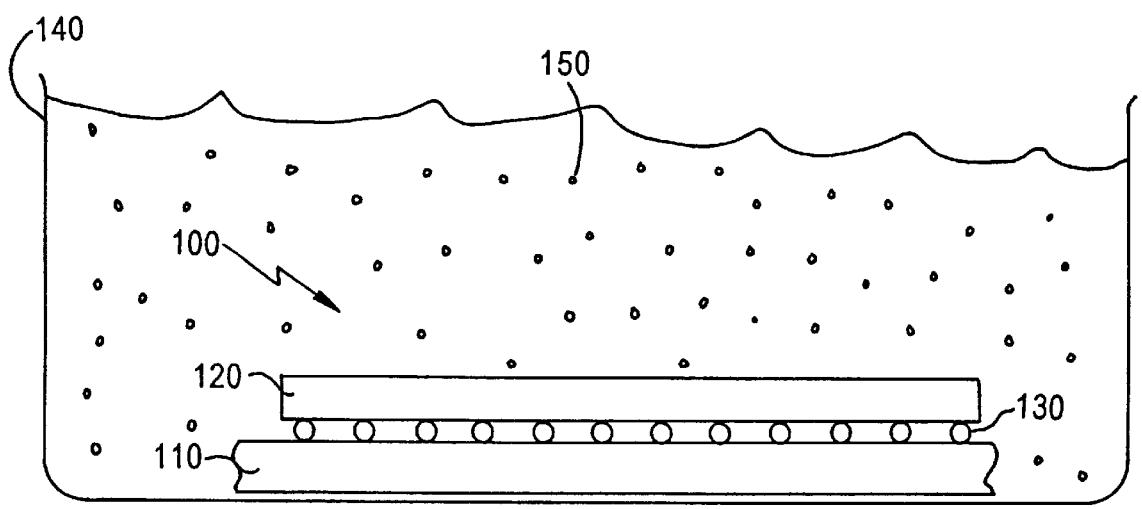
FIG. 1 is a side view of a semiconductor package assembly to be inspected by the present invention.

An embodiment of the present invention will now be described with reference to FIGS. 1–3. As shown in FIG. 1, a semiconductor package assembly 100 to be inspected comprises a substrate 110 with bonding pads (not shown), such as round metallic bonding pads, a semiconductor device 120 with corresponding bonding pads (not shown), and solder bumps 130 attached, as by reflowing in an oven, between each substrate bonding pad and its corresponding bonding pad of semiconductor device 120. The following procedure is performed on package assembly 100 either before or after stress testing, such as heat cycling.

Figure 2:
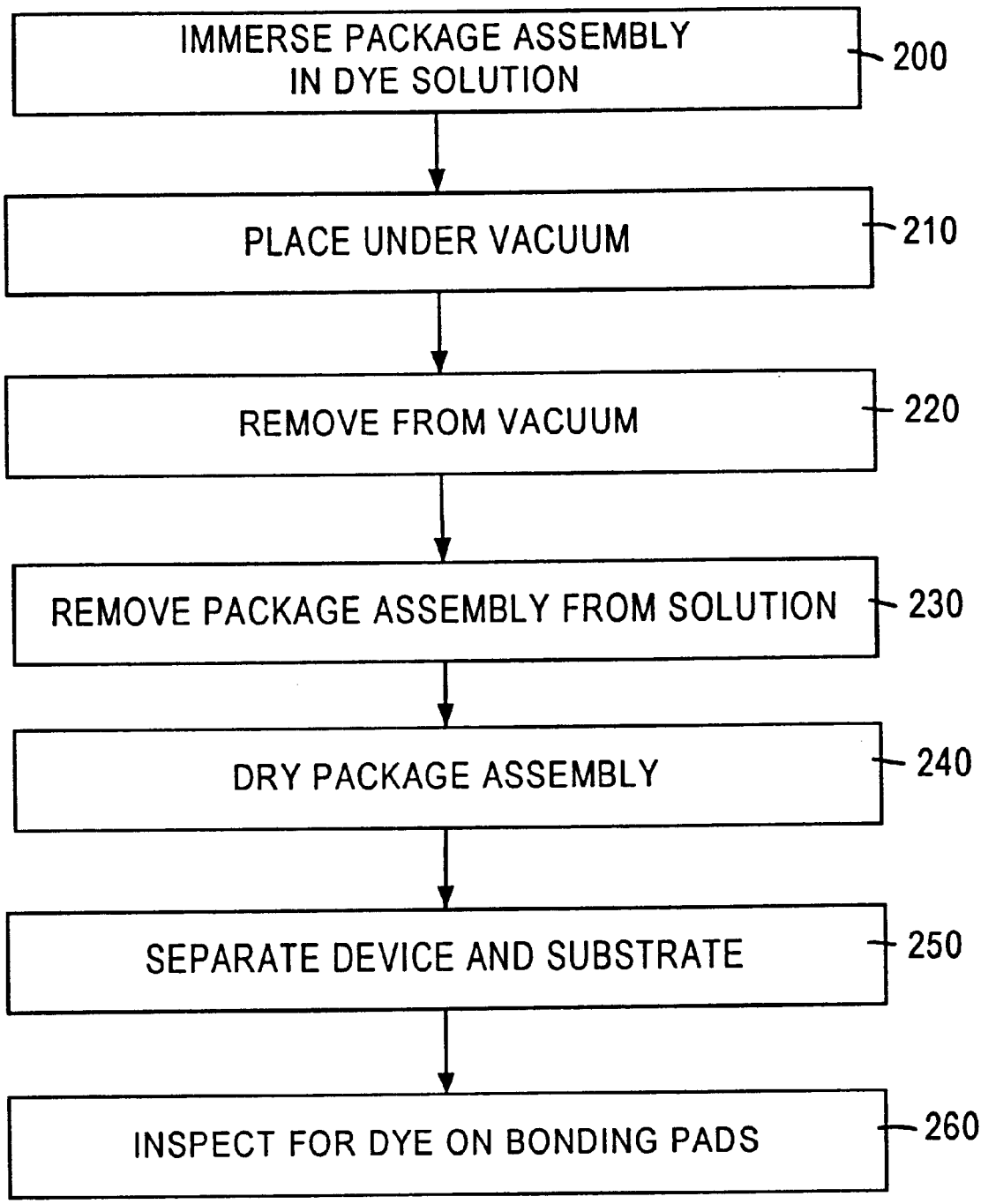
FIG. 2 is a flow chart of a method according to an embodiment of the present invention.
Figure 3:
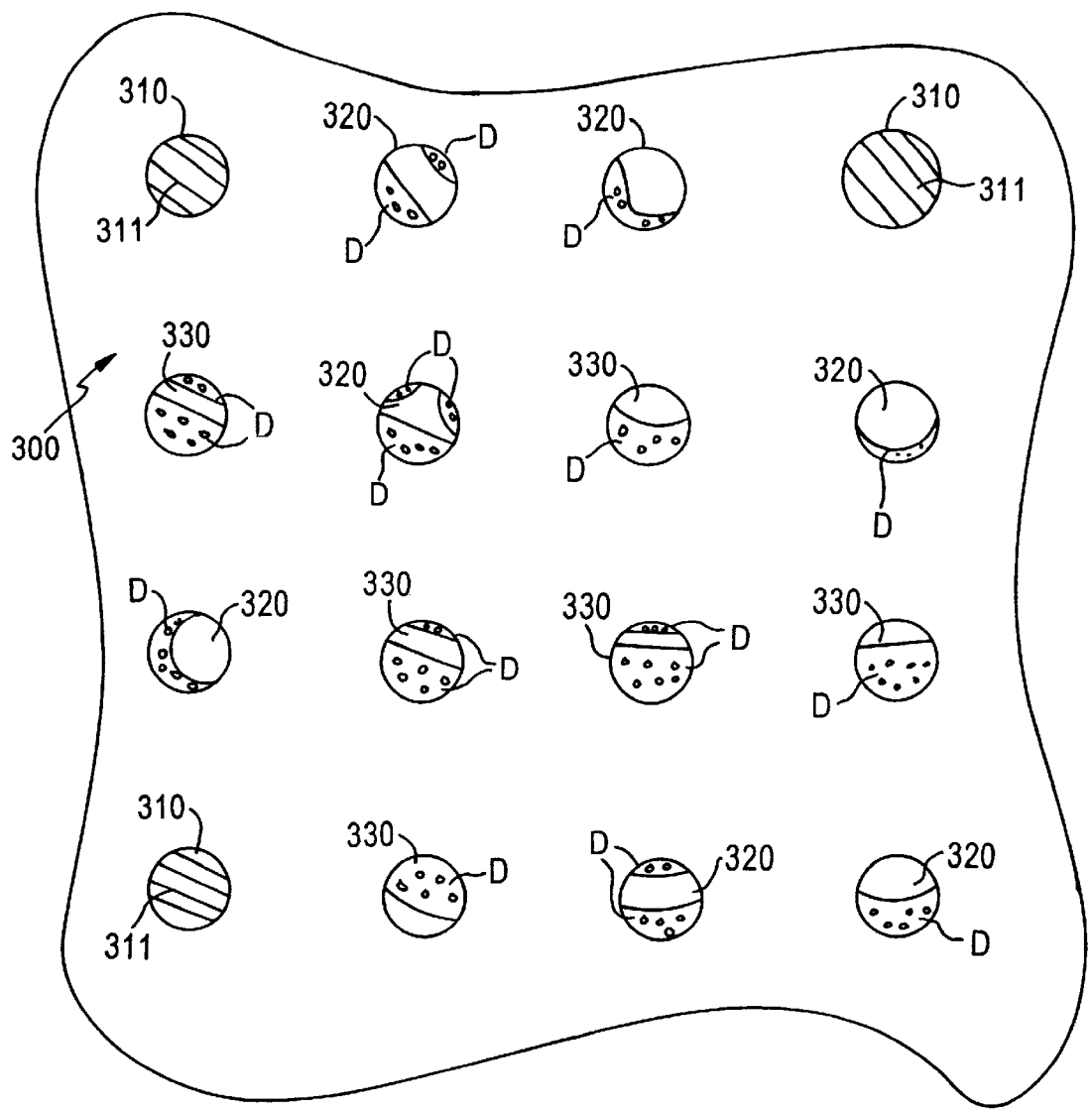
FIG. 3 is a top view of bonding pads inspected according to an embodiment of the present invention.

Referring now to FIG. 1 and the flow chart of FIG. 2, at step 200, package assembly 100 is placed in a container 140, such as a beaker or a petri dish, and immersed in a solution of dye 150, preferably a dye which can be photographed with white light, such as a conventional red tracer dye used in machining and available from Valley Tool of Milpitas, Calif. Dye solution 150 preferably completely covers package assembly 100. At step 210, the immersed package assembly is put in a conventional vacuum chamber and placed under a vacuum, such as about −27 inches of mercury for about one hour, such that when cracks exist between solder bumps 130 and the substrate bonding pads, or between solder bumps 130 and the semiconductor device bonding pads, dye solution 150 flows into the cracks.

Next, at step 220 package assembly 100 is removed from the vacuum, then removed from the vacuum chamber and dye solution 150 (see step 230) and dried, as by drip-drying and towel-drying followed by heating in a conventional drying oven at about 125 degrees Centigrade for about 2 hours (see step 240), resulting in the dye from dye solution 150 remaining to stain substrate 110 and semiconductor device 120. Semiconductor device 120 is thereafter separated from substrate 110 at step 250, preferably by manually prying off semiconductor device 120 (e.g., with a fingernail), thereby exposing some of the bonding pads. The solder joints will break at their weakest points, typically separating from semiconductor device 120 and remaining adhered to substrate 110. After separation, any loose solder bumps 130 are removed from substrate 110 and semiconductor device 120, preferably manually. However, solder bumps 130 are preferably not forced off the bonding pads, to avoid smearing the remaining dye.

At step 260, the substrate bonding pads and/or the semiconductor device bonding pads are inspected for the dye, thereby locating the cracks. Inspection is preferably carried out with an optical microscope at about 150 power. FIG. 3 is an example of an array of bonding pads 300 of substrate 110 or of semiconductor device 120 after separation step 250. Some bonding pads 310 have solder bumps 311 still attached, indicating that solder bumps 311 have properly adhered to bonding pads 310. Other bonding pads 320 are partially stained with dye D, indicating partial cracks in these solder joints due to improper solder wetting during reflow, or stress induced during heat cycling. Still other bonding pads 330 are almost completely covered with dye D, indicating a crack occurred all the way across pads 330.

The methodology of the present invention enables reliable and accurate inspection of the adhesion of all the solder bumps of any package assembly to bonding pads of a substrate and a packaged semiconductor device, and can be performed prior to or after stress testing. The present invention thereby facilitates thorough testing of the performance of the solder reflow process and evaluation of the wetting of the solder to the pads.

The present invention is applicable to the manufacture of various types of solder-bumped semiconductor package assemblies, particularly FGBAs.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method of inspecting solder joints of a semiconductor package assembly, the package assembly comprising a substrate with bonding pads, a semiconductor device with bonding pads, and solder bumps attached between each substrate bonding pad and a corresponding bonding pad of the semiconductor device, the method comprising:

immersing the package assembly in a solution comprising dye;

placing the immersed package assembly under a vacuum such that, when cracks exist between the solder bumps and substrate bonding pads, or between the solder bumps and the semiconductor device bonding pads, the dye solution flows into the cracks;

removing the package assembly from the vacuum and the dye solution;

drying the package assembly;

separating the semiconductor device and the substrate to expose a plurality of the substrate bonding pads or the semiconductor device bonding pads; and inspecting the exposed bonding pads for the dye, thereby locating the cracks.

2. The method of claim 1, comprising immersing the package assembly in a solution comprising red tracer dye.

3. The method of claim 1, comprising placing the immersed package assembly under a vacuum of about −27" Hg.

4. The method of claim 3, comprising placing the immersed package assembly under the vacuum for at least one hour.

5. The method of claim 1, comprising drying the package assembly in an oven at about 125 degrees Centigrade for about 2 hours.

6. The method of claim 1, comprising inspecting the substrate bonding pads and the semiconductor device bonding pads with an optical microscope.

7. The method of claim 6, comprising inspecting with an optical microscope at a power of about 150x.

8. The method of claim 1, comprising manually separating the semiconductor device and the substrate.

9. The method of claim 1, comprising temperature cycling the package assembly prior to immersing the package assembly in the dye solution.

\* \* \* \* \*